(12) United States Patent
Silich (10) Patent No.: US 7,799,000 B2
(45) Date of Patent: Sep. 21, 2010

(54) FIXATION APPARATUS FOR A MEDICAL DEVICE

(75) Inventor: Bert Silich, Harrison Township, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 12/302,608

(22) PCT Filed: Jun. 1, 2007

(86) PCT No.: PCT/US2007/070226

§ 371 (c)(1),
(2), (4) Date: May 5, 2009

(87) PCT Pub. No.: WO2007/143555

PCT Pub. Date: Dec. 13, 2007

(65) Prior Publication Data

US 2009/0287155 A1  Nov. 19, 2009

Related U.S. Application Data

(60) Provisional application No. 60/810,197, filed on Jun. 1, 2006.

(51) Int. Cl.
*A61M 5/32* (2006.01)

(52) U.S. Cl. .......... 604/174; 604/177; 604/179
(58) Field of Classification Search .......... 604/174, 604/175, 177, 178, 179, 513
See application file for complete search history.

(56) References Cited

U.S. PATENT DOCUMENTS

| | | | |
|---|---|---|---|
| 4,683,895 A * | 8/1987 | Pohndorf | 606/232 |
| 5,318,543 A | 6/1994 | Ross et al. | |
| 5,957,968 A | 9/1999 | Belden et al. | |
| 6,901,287 B2 * | 5/2005 | Davis et al. | 607/2 |
| 2004/0176781 A1 * | 9/2004 | Lindstrom et al. | 606/129 |

* cited by examiner

*Primary Examiner*—Kevin C Sirmons
*Assistant Examiner*—Bhisma Mehta
(74) *Attorney, Agent, or Firm*—Brooks Kushman P.C.

(57) ABSTRACT

A fixation apparatus for attaching a medical device to a patient includes an attachment feature attached to the medical device and configured to cooperate with one or more surgical staples to facilitate stapling of the medical device to the patient. The attachment feature includes a staple receiving portion including two ends, each of which has a staple retaining end disposed adjacent thereto. The staple receiving portion is configured to receive surgical staples, and the staple retaining ends are configured to inhibit the staple receiving portion from dislodging from the surgical staples.

25 Claims, 6 Drawing Sheets

FIXATION APPARATUS FOR A MEDICAL DEVICE

CROSS-REFERENCE TO RELATED APPLICATIONS

This application claims the benefit of U.S. provisional application Ser. No. 60/810,197 filed on 1 Jun. 2006, which is hereby incorporated herein by reference.

BACKGROUND OF THE INVENTION

1. Field of the Invention

The present invention relates to a fixation apparatus for a medical device, and in particular, a fixation apparatus for attaching a medical device to a patient.

2. Background Art

In the field of medicine, inadvertent needle sticks are an omnipresent hazard to both medical personnel and patients. One way to reduce the probability of an accidental needle stick is to reduce the number of needles used in medical procedures. For example, surgical staples have been shown to be a viable alternative to traditional sutures for closing certain incisions. The use of anchoring devices such as surgical staples as a mechanism for attaching a medical device to a patient is, however, far from fully developed. For example, a venous or arterial catheter may be inserted into a patient and left there for an extended period of time. In order to inhibit accidental removal of the catheter, a catheter clamp, or even the catheter hub, is often attached to the patient's skin. The catheter hub is a device used with multi-lumen catheters that allows multiple input lines to feed into a main catheter line. The other ends of the input lines may be attached to sources of medicinal liquids that are provided to the patient through the main catheter line. The catheter hub generally has a fixed location relative to the point of entry of the catheter line into the patient. In contrast, a catheter clamp is a device that is generally movable relative to the catheter line, so it may be conveniently attached to the line near its point of entry into the patient. The attachment of the catheter clamp or catheter hub to the patient provides strain relief, such that if the catheter line is inadvertently tensioned, the strain will be at the point of attachment to the patient, and the end of the catheter will not be dislocated.

To facilitate attachment of a catheter hub or catheter clamp to a patient, one or more holes are typically provided in the device so that medical personnel can suture the hub or clamp directly to the patient's skin. As an alternative to the suture, it has been recommended that a surgical staple be used, utilizing the same hole that was specifically designed to receive the sutures. This system has generally proven inadequate, in that installing a surgical staple through a hole that was specifically designed to accommodate sutures is awkward, and to the extent that medical personnel are successful at installing a staple through such a hole, the attachment may be inadequate. For example, it may be necessary to not only staple both sides of the hub or clamp to provide adequate fixation, it may be necessary to use more than one staple in each hole. This means that medical personnel may be required to perform the cumbersome operation of stapling through a suture hole four or more times to secure one catheter line.

Therefore, a need exists for a fixation apparatus for attaching a medical device, such as a catheter clamp, to a patient that facilitates the use of non-suture anchoring devices, such as surgical staples, to be used as the primary or sole form of fixation, and that allows such anchoring devices to be easily attached while still securely affixing the medical device to the patient.

SUMMARY OF THE INVENTION

Embodiments of the present invention provide a fixation apparatus for attaching a medical device to a patient using a non-suture anchoring devices, such as one or more surgical staples.

Embodiments of the invention also provide a fixation apparatus for attaching a medical device to a patient that readily accommodates the use of surgical staples such that they are easy to install and remove, and yet firmly affix the medical device to the patient.

One embodiment of the present invention includes a two-piece catheter clamp that can be positioned at a plurality of locations along a catheter line. An inner portion of the clamp snaps onto the catheter line, while an outer portion of the clamp snaps onto the inner portion, causing the inner portion to securely grip the catheter line. The outer portion of the catheter clamp includes a pair of attachment features, each of which is characterized by an elongate portion configured to receive one or more surgical staples, and a pair of staple retaining ends, each of which is attached to a respective one of the elongate portions. The elongate portions are sized to receive surgical staples, such that a staple will wrap around the elongate portion as it is installed into the skin of a patient. In this embodiment, the attachment features are disposed on opposite sides of the outer portion of the clamp, and therefore, one staple wrapped around each of the elongate portions can firmly affix the catheter clamp to the patient. With this configuration, the staple retaining ends may be optional, in that movement of the catheter clamp that would otherwise dislodge the clamp from the staple on one side, would be inhibited by the staple on the other side.

In one embodiment, a hole is added through each of the attachment features to provide medical personnel the option of using sutures in addition to, or as an alternative to, the surgical staples. To the extent that surgical staples are used, the cross section of each attachment feature is specifically configured to facilitate the use of a staple remover to remove the staple. In particular, a transverse cross section through the elongate portion of each of the attachment features, includes two portions. The first, a base portion, is that portion immediately adjacent the skin of the patient. The second portion is above the base portion, and has a width that is less than the width of the base portion. This leaves open areas on either side of the second portion, just above the base portion, where a standard two-pronged staple remover can be inserted.

In some embodiments of the present invention, the cross section of the elongate members is generally uniform. In other embodiments, however, the cross section changes along the length of the elongate member. Moreover, because there are many different types of surgical staples available, the staple receiving elongate portions of the present invention can be configured with cross sections specifically designed to accommodate certain types of staples. In addition to being configured for specific types of staples, embodiments of the present invention may include staple receiving portions that are tapered. Such a staple receiving portion can be tapered in one or both directions as seen from a top view of the fixation apparatus, it can be tapered in one or both directions as viewed from a side view of the fixation apparatus, or alternatively, it can be tapered in both a top and side view. These configurations allow flexibility with regard to the choice of staples. For example, larger staples can be attached at the larger portions of the taper, whereas narrower portions of the taper can be used to accommodate smaller staples. It is worth noting that the "taper" of the staple receiving portion need not be uniform or constant along its length. Rather, such a taper can include discrete stepped changes in dimension, and the dimension or dimensions may change from larger to smaller and back to smaller, or vice versa.

Embodiments of the invention also provide a fixation apparatus for attaching a medical device to a patient. The fixation apparatus includes an attachment feature attached to the medical device and configured to cooperate with at least one surgical staple to facilitate stapling of the medical device to the patient. The attachment feature includes a staple receiving portion having a first dimension and including two ends. The staple receiving portion is configured to receive the at least one surgical staple. The at least one staple can be installed around the staple receiving portion or a part thereof. Also included are first and second staple retaining ends, respectively disposed adjacent one of the ends of the staple receiving portion. Each of the staple retaining ends is configured with a second dimension greater than the first dimension of the staple receiving portion, thereby inhibiting the staple receiving portion from dislodging from the at least one staple when the at least one staple is received by the staple receiving portion.

Embodiments of the invention further include a catheter clamp, including a tube retaining portion configured to receive a catheter line therein. An attachment feature is attached to the tube retaining portion, and is configured to cooperate with at least one surgical staple to facilitate stapling of the tube retaining portion to the patient. The attachment feature includes a staple receiving portion having proximal and distal ends and a first dimension. The staple receiving portion is configured to receive the at least one surgical staple. The proximal end abuts the tube retaining portion. A retaining end is disposed adjacent the distal end of the staple receiving portion. The retaining end is configured with a second dimension greater than the first dimension of the staple receiving portion, thereby inhibiting the staple receiving portion from becoming dislodged from the at least one staple.

Embodiments of the invention also include a catheter kit, including a package for housing contents of the kit, and a plurality of medical devices disposed within the housing for use in the installation of an indwelling catheter. The medical devices include a catheter clamp, which includes a tube retaining portion configured to receive a catheter line therein. The clamp also includes an attachment feature attached to the tube retaining portion and configured to cooperate with at least one surgical staple to facilitate stapling of the tube retaining portion to a patient. The attachment feature may be configured as described above.

Embodiments of the invention further include a method of installing an indwelling catheter in a patient, and fixing the catheter to the patient using a catheter clamp having a tube receiving portion, and a staple receiving portion. The staple receiving portion includes proximal and distal ends, and is configured to receive at least one surgical staple. The proximal end abuts the tube receiving portion, and the catheter clamp further includes a retaining end disposed adjacent the distal end of the staple receiving portion. The method includes selecting a catheter, selecting a place for entry on the patient, inserting the catheter using the Seldinger technique, and securing the catheter to the patient. Securing the catheter to the patient includes the step of disposing at least one surgical staple around at least a portion of the staple receiving portion of the catheter clamp, such that a closed length of the at least one staple is less than a dimension of the retaining end of the catheter clamp. In this way the staple receiving portion is inhibited from dislodging from the at least one staple.

DETAILED DESCRIPTION OF THE PREFERRED EMBODIMENT(S)

Figure 1:
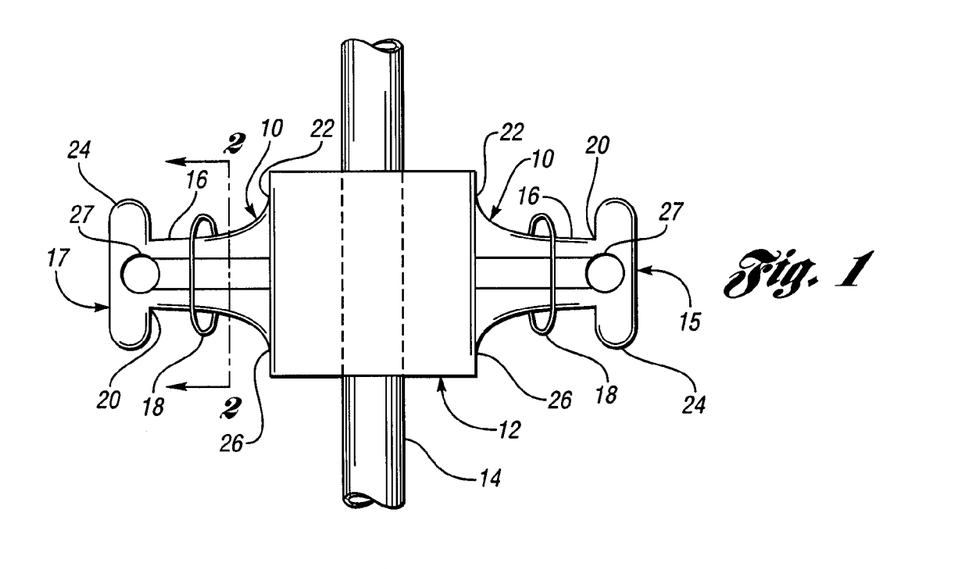
FIG. 1 is a top plan view of a catheter clamp and fixation apparatus in accordance with one embodiment of the present invention.

FIG. 1 shows a top plan view of a fixation apparatus 10 in accordance with one embodiment of the present invention. The fixation apparatus 10 provides a fast and efficient mechanism for securing a medical device, such as catheter clamp 12, to a patient using a non-suture anchoring device, such as a surgical staple. Although surgical staples are illustrated and described in the proceeding examples, embodiments of the present invention may be used with other non-suture anchoring devices, such as the device described in U.S. Pat. No.

5,792,115 issued to Horn on 11 Aug. 1998, which is hereby incorporated herein by reference. Moreover, as described below, embodiments of the invention may also accommodate sutures to be used in conjunction with non-suture anchoring devices.

The present invention is not limited to fixation apparatuses used with catheter clamps, but may be used with other medical devices, such as chest tubes, arterial lines, PEG tubes, and surgical drains. As described in detail below, in conjunction with FIGS. 13 and 14, the medical device may be a suture or sutures tied around a portion of the fixation apparatus. In addition to externally fixated devices, embodiments of the present invention may be used for fixation of internal devices, for example, a device affixed to a patient's bone. Indeed, the present invention is not limited to medical devices used with human patients, but may be used in conjunction with devices used in veterinary medicine.

The catheter clamp 12 is configured to secure a catheter line 14 such that the end of the catheter line (not shown) will not be inadvertently removed from the patient. The fixation apparatus 10 includes a first attachment feature, or wing 15, and a second attachment feature, or wing 17, as viewed in FIG. 1. The wings 15, 17 are configured to cooperate with the catheter clamp 12, and in the embodiment shown in FIG. 1 are integrally formed with it. Because the wings 15, 17 are essentially mirror images of each other, their respective component parts are provided with the same label numbers. Each of the wings 15, 17 of the fixation apparatus 10 includes an anchor receiving portion, or staple receiving portion, 16. In the embodiment shown in FIG. 1, the staple receiving portion 16 is a generally elongate member, configured to receive one or more non-suture anchoring devices, such as staples 18.

The staple receiving portions 16 each have distal and proximal ends 20, 22, respectively. Anchor retaining ends, or staple retaining ends, 24, 26 are respectively disposed adjacent the ends 20, 22 of the staple receiving portions 16. As explained in more detail below, the staple retaining ends 24, 26 are configured to inhibit the staple receiving portions 16 from dislodging from the staples 18. In the embodiment shown in FIG. 1, the staple retaining end 26 includes a portion of the clamp 12. In other embodiments, or when used with medical devices other than catheter clamps, a fixation apparatus in accordance with the present invention may have two staple retaining ends, both of which are separate from the medical device. It is also worth noting that although the fixation apparatus 10, shown in FIG. 1, includes two wings 15, 17, other embodiments contemplated by the present invention may include only one such wing, or more than two wings.

Although the fixation apparatus 10 is configured to conveniently and effectively receive surgical staples to secure to a patient a medical device, such as the catheter clamp 12, apertures 27 are nonetheless provided to give medical personnel the option of a more conventional attachment mechanism, for example, sutures. Although the apertures 27 are illustrated in FIG. 1 as round holes, it is understood that they may be any shape or size effective to facilitate attachment of the catheter clamp 12 to a patient—with a suture or non-suture anchoring device. To the extent that surgical staples, such as the staples 18, are used to affix the clamp 12 to a patient, the fixation apparatus 10 is configured to provide for easy removal of such staples.

Figure 2:
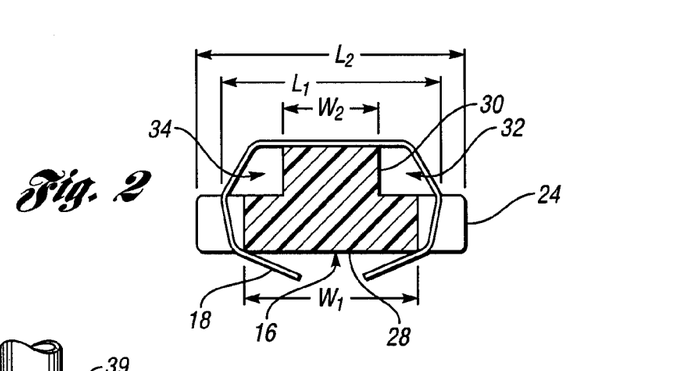
FIG. 2 is a cross-sectional view of a portion of the fixation apparatus shown in FIG. 1, taken through lines 2-2.

FIG. 2 shows a cross section of the wing 17 of the fixation apparatus 10. As shown in FIG. 2, the staple receiving portion 16 includes first and second portions 28, 30. The first portion 28 has a first dimension, or width ($W_1$), and the second portion 30 has a width ($W_2$) that is less than the width of the first portion 28. As shown in FIG. 2, the second portion 30 is disposed away from the patient relative to the first portion 28 such that this creates open spaces or areas 32, 34 between the staple receiving portion 16 and the staple 18. The open spaces 32, 34 provide access for a staple removing tool, thereby facilitating removal and/or repositioning of the catheter clamp 12. Although the specific widths ($W_1$), ($W_2$) can be any size effective to provide a fixation apparatus suitable for its intended purpose, a dimension for ($W_1$) of approximately 0.125 inches, and a dimension for ($W_2$) of 0.030 inches, has been found to be effective for a staple receiving portion used on a catheter clamp. In addition, the staple 18 has a closed length denoted as ($L_1$), which is greater than the width ($W_1$). This allows a staple remover to be inserted in the space between the first portion 28 and the staple 18, which may be particularly convenient for configurations not having the stepped cross section shown in FIG. 2.

Of course, in addition to the width of the staple receiving portion 16, the height may also be important. For example, using the width dimensions given above, an overall height of 0.050 inches has been found to be effective for a catheter clamp, such as the clamp 12. Adjusting the height of the first portion 28 relative to the height of the second portion 30 will also provide more or less open area 32, 34 in which a staple removing device can be inserted. In one example, the overall height of 0.050 inches can be divided such that the first portion 28 has a height of only 0.010 inches, leaving the remaining 0.040 inches for the second portion 30, and the open spaces 32, 34. Although the first and second portions 28, 30 are shown as generally rectangular in the embodiment shown in FIG. 2, they may be configured with other shapes. For example, to accommodate a curved staple, the top portion 30 may be configured with a curved surface, rather than a straight surface.

As discussed above in conjunction with FIG. 1, the staple retaining ends 24, 26 help to keep the staple receiving portions 16 from being dislodged from the staples 18. FIG. 2 illustrates this feature. For example, the staple retaining end 24 has a second dimension, or length ($L_2$), that is greater than ($W_1$) and greater than ($L_1$). In this way, the staple receiving portion 16 is inhibited from sliding out from under the staple 18 if there is a sliding fit between the staple receiving portion 16 and the staple 18. In general, it is readily discernable from the remaining drawing figures that for the various embodiments illustrated, a retaining end has a dimension—e.g., the length ($L_2$)—that is greater than a dimension of the anchor receiving portion—e.g., the width ($W_1$)—and that this difference in dimensions inhibits the anchor receiving portion from dislodging from the anchor. Although the dimension of the anchor receiving portion 16 is referred to as a width, and the dimension of the retaining end 24 is referred to as a length, it is understood that these dimensions may be diameters, thicknesses, heights, etc., the nomenclature partly depending on the orientation of the apparatus in the particular drawing figure.

Figure 3:
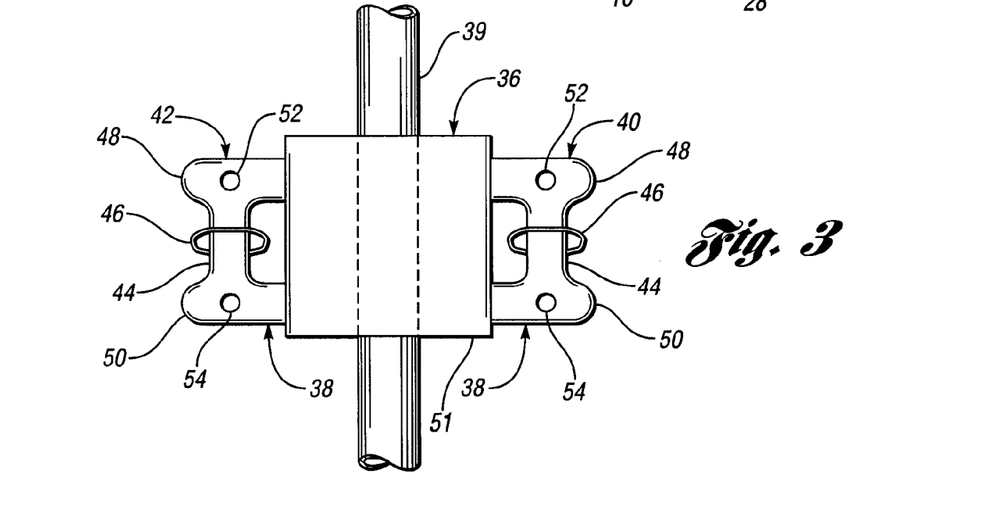
FIG. 3 is a top plan view of a catheter clamp and fixation apparatus in accordance with a second embodiment of the present invention.

FIG. 3 shows a catheter clamp 36 and a fixation apparatus 38 in accordance with another embodiment of the present invention. The catheter clamp 36 is configured to secure a catheter line 39 to a patient. It is worth noting that although FIGS. 1-3 illustrate the use of fixation apparatuses 10, 38 used in conjunction with the same medical device—i.e., a catheter clamp—this need not be the case. As described above, fixation apparatuses in accordance with the present invention can be used with other medical devices to provide a fast and effective mechanism for stapling the device securely to a patient. As with the fixation apparatus 10 shown in FIG. 1, the fixation apparatus 38 shown in FIG. 3 includes attachment features 40, 42.

Each of the attachment features 40, 42 includes a staple receiving portion 44 configured to receive one or more surgical staples 46. In addition, they each include two staple retaining ends 48, 50. Unlike the embodiment shown in FIG. 1, where one of the staple retaining ends 26 was the body of the catheter clamp 12, the staple retaining ends 48, 50 are separate from a body portion 51 of the catheter clamp 36. Of course, the fixation apparatus 38 still forms a portion of the catheter clamp 36, and may be integrally molded with the body portion 51. Because of their profile in the top view shown in FIG. 3, each of the attachment features 40, 42 may be referred to as a "dog bone".

Similar to the staple receiving portion 16 shown in FIGS. 1 and 2, the staple receiving portions 44 can be configured with various cross sections, for example, to accommodate a staple remover, such as shown in FIG. 2. In addition, each of the dog bones 40, 42 includes apertures 52, 54. Again, this provides medical personnel with an option when determining the type of fixation—for example, the use and location of suture and non-suture anchors. Although each of the left and right dog bones 40, 42 includes two apertures 52, 54, a single aperture, or more than two apertures, can be used. The same applies to the fixation apparatus 10 shown in FIG. 1, which could include more than one aperture in each of the wings 15, 17. Such apertures may be disposed in any location and may be of any geometric configuration effective to facilitate attachment.

Figure 4A:
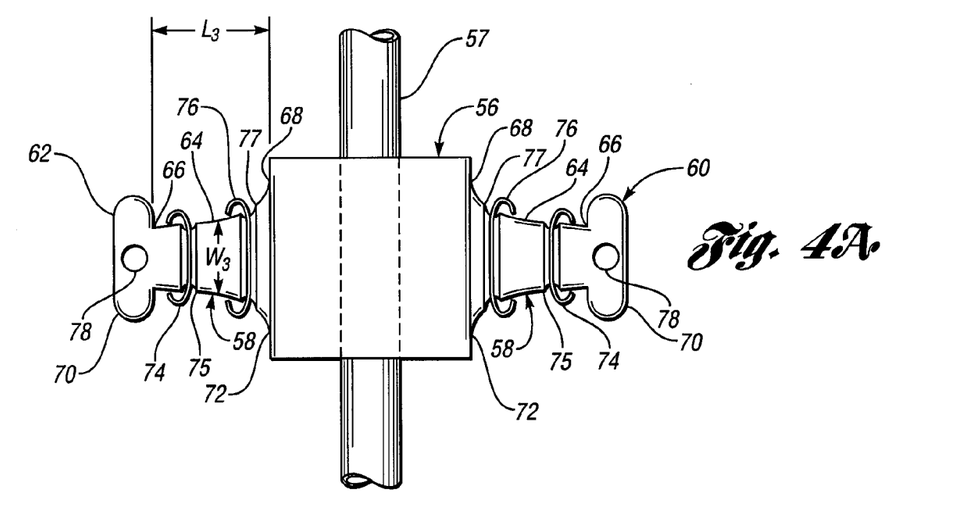
FIG. 4A is a top plan view of a catheter clamp and fixation apparatus in accordance with a third embodiment of the present invention.

FIG. 4A shows a top plan view of a catheter clamp 56 and a fixation apparatus 58 in accordance with a third embodiment of the present invention. The catheter clamp 56 is configured to secure a catheter line 57 to a patient. The fixation apparatus 58 is similarly configured to the previously described fixation apparatuses 10, 38, in that it includes attachment features 60, 62. Each of the attachment features 60, 62 includes a staple retaining portion 64 having two ends 66, 68. There are also two staple retaining ends 70, 72 disposed adjacent the ends 66, 68 of the staple receiving portion 64.

As shown in FIG. 4A, the staple receiving portions 64 are tapered from a large size at their respective proximal end 68, to a smaller size at their respective distal end 66. In other embodiments, the taper can be reversed. The tapered configuration provides medical personnel with the option of using a number of different sizes of staples. For example, in some situations small staples 74 may be the only ones available. In which case, they can be applied to the staple receiving portion 64 near the distal end 66. Similarly, where only a larger size staple 76 is available, the catheter clamp 56 can be secured to the patient using the larger staples 76 attached near the proximal end 68.

One way to describe the tapers of the staple receiving portions 64 is as follows—for illustrative purposes, only one of the tapers shown in FIG. 4A is labeled and so described. The staple retaining ends 70, 72 define a length ($L_3$) along the staple receiving portion 64. If a cross section of the staple receiving portion 64 is taken in a direction perpendicular to the length ($L_3$), a width—shown in one location as $W_3$—will vary depending on where along the length ($L_3$) the cross section is taken.

Also shown in the embodiment in FIG. 4A, are grooves 75, 77 that are formed within the staple receiving portions 64. These grooves provide a discrete location for installation of the staples 74, 76, and also help to inhibit lateral movement of the clamp 56. As with the other embodiments, apertures 78 are provided to facilitate a secondary or alternative attachment mechanism. In some embodiments, grooves, such as the grooves 75, 77, can be sized to hold a staple in place prior to its being fixed to a patient. Specifically, such a groove can be sized to have a snap-fit with a staple. In such embodiments, a staple applicator, a staple, and a medical device—such as the catheter clamp 56—can be preassembled, with the staple retained by a groove in the fixation device associated with the medical device. This provides a fast and convenient attachment system, in that medical personnel need not work with separate components. Rather, the staple applicator carries the staple, and by virtue of the groove, the medical device; the applicator is used to position the medical device, and the applicator is actuated to fix the staple to the patient.

Figure 4B:
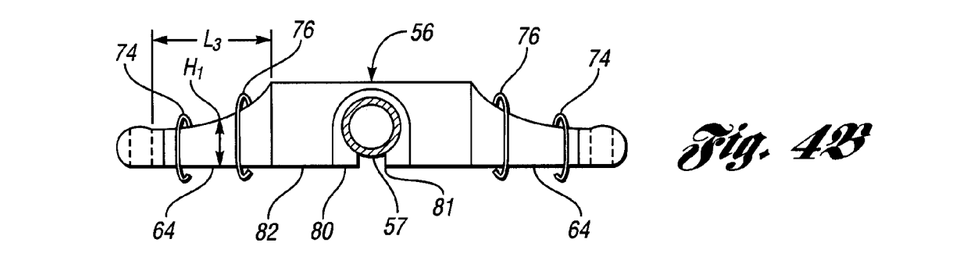
FIG. 4B is a front plan view of the catheter clamp and fixation apparatus shown in FIG. 4A.

FIG. 4B shows a front plan view of the catheter clamp 56 and fixation apparatus 58 shown in FIG. 4A. As shown in FIG. 4B, each of the staple receiving portions 64 is not only tapered as seen from a top view, but is also tapered as seen from a front view. Again, this is indicative of the flexibility of a fixation apparatus in accordance with the present invention, which may have cross sections that provide specific advantages. For example, as described above, a tapered cross section can facilitate the use of different sizes of staples. Moreover, a tapered cross section can reduce the amount of material needed to manufacture the device, thereby saving production costs. In this view, it is shown that a cross section taken in a direction perpendicular to the width—see, e.g., width ($W_3$) shown in FIG. 4A—will have a variable height, shown in one location as $H_1$.

In general, fixation apparatuses such as the fixation apparatuses 10, 38, 58 described above, can be made from any material effective to allow the fixation apparatus to perform its intended use. Of course, it may be advantageous to use materials that meet medical standards for sterilization. Some examples of materials that could be use are: polymers or composites such as polypropylene, polyethylene, polycarbonate, polyvinyl chloride, acrylonitrile butadiene styrene (ABS), acrylic, polyester, olefin, nylon, as well as other types of thermosetting or thermoplastic polymers may be used. Moreover, metals such as stainless steel, cobalt chromium alloys, titanium alloys, etc. can be used, or some combination of different materials, such as metals and polymers.

As shown in FIG. 4B, the catheter clamp 56 includes two portions: a flexible inner portion 80, and a more rigid outer portion 82. Thus, it may be desirable to manufacture the clamp 56 from more than one material. The inner portion 80 includes an opening 81 that allows the inner portion 80 to be snapped onto the catheter line 57 at some desired location. The outer portion 82 is then placed over the inner portion 80 such that the inner portion 80 firmly grips the catheter line 57. This two-piece construction is well known to those in the art. Thus, the fixation apparatus 58 is formed as part of the outer portion 82 of the clamp 56, and the inner portion 80 of the clamp 56 can be a standard inner portion useable with catheter clamps not having the advantageous fixation apparatus of the present invention.

Figure 5:
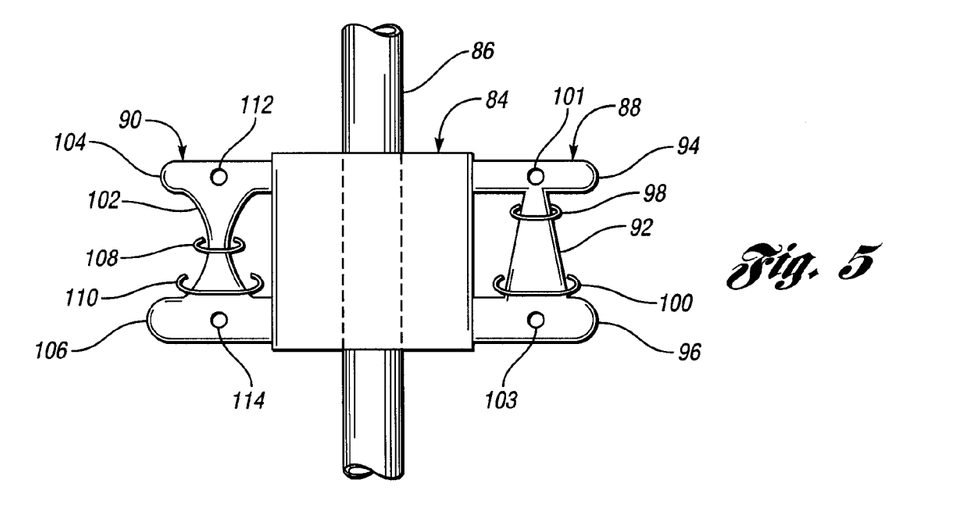
FIG. 5 is a top plan view of a catheter clamp illustrating alternative embodiments of fixation apparatuses to be used therewith.

FIG. 5 shows a catheter clamp 84 used to attach a catheter line 86 to a patient. In the embodiment shown in FIG. 5, the catheter clamp 84 includes two separate fixation apparatuses 88, 90. In practice, such asymmetrical fixation apparatuses would likely not be used; however, the two apparatuses 88, 90 are shown here on the same clamp 84 for illustrative purposes. The fixation apparatus 88 includes a staple receiving portion 92 and two staple retaining ends 94, 96. The staple retaining ends can be symmetric, such as shown in FIG. 3, or asymmetric, such as shown in FIG. 5. Similar to the embodiment shown in FIGS. 4A and 4B, the staple receiving portion 92 is tapered, allowing it to receive staples 98, 100 of different sizes. In addition, apertures 101, 103 are provided as a secondary or alternative means of securing the clamp 84 to the patient.

The fixation apparatus 90 also includes a staple receiving portion 102 and staple retaining ends 104, 106, which, in the embodiment shown in FIG. 5, are asymmetric. The staple receiving portion 102 has an hour glass shape, which allows a smaller staple 108 to be placed around a middle portion, and also accommodates larger staples 110, which can be placed near the staple retaining ends 104, 106. Apertures 112, 114 are also provided.

Figure 6:
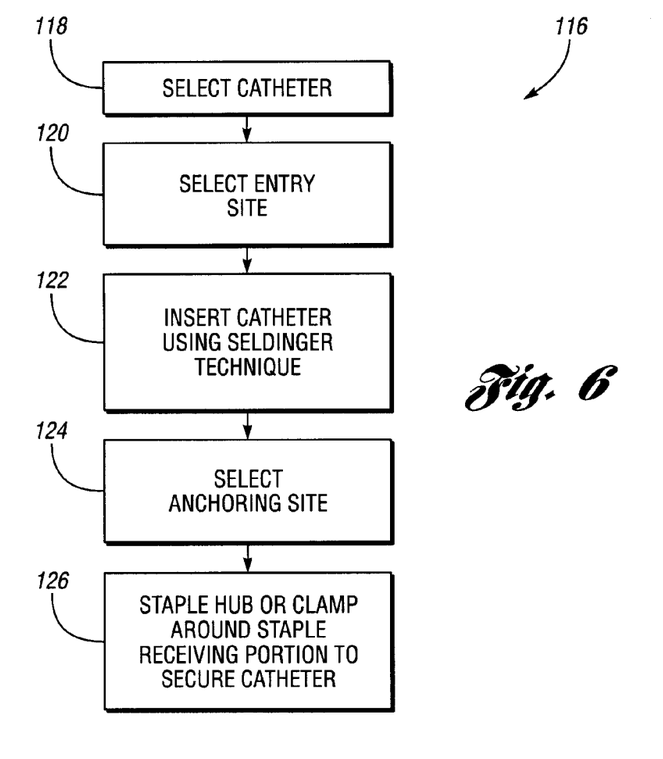
FIG. 6 is flowchart illustrating a method of installing an indwelling catheter in a patient in accordance with one embodiment of the present invention.

FIG. 6 shows a flowchart 116 illustrating a method of installing an indwelling catheter in accordance with the present invention. At step 118, a medical personnel, typically a doctor, will choose an appropriate catheter. This may be a central venous catheter, a cardiac catheter, an arterial catheter, or other appropriate catheter for the patient. At step 120, the doctor selects an appropriate entry site into the patient. For example, this may be through the patient's torso, groin area, or extremity. At step 122, the catheter is inserted using the Seldinger technique. This involves a number of steps well known to those in the medical field. At step 124, an anchoring site is selected. This may be the site at which the catheter hub will be anchored, or it may be the site at which a variable position catheter clamp is anchored. In either case, the doctor chooses the site at which the catheter line will be secured to the patient.

At step 126, the hub or clamp is stapled with one or more surgical staples being disposed around a staple receiving portion of a fixation apparatus, for example, as in the fixation apparatuses 10, 38, 58, 88, 90 as described above. In addition, one or more sutures can be placed through various apertures in the fixation apparatus. The use of sutures with the fixation apparatuses of the present invention may be optional, in that the fixation apparatuses provide an efficient and effective means for securing medical devices to the patient using surgical staples alone. Although the method described above is specific to installing a catheter, it is understood that the present invention contemplates methods of installing other medical devices, for example, those described above.

Figure 7:
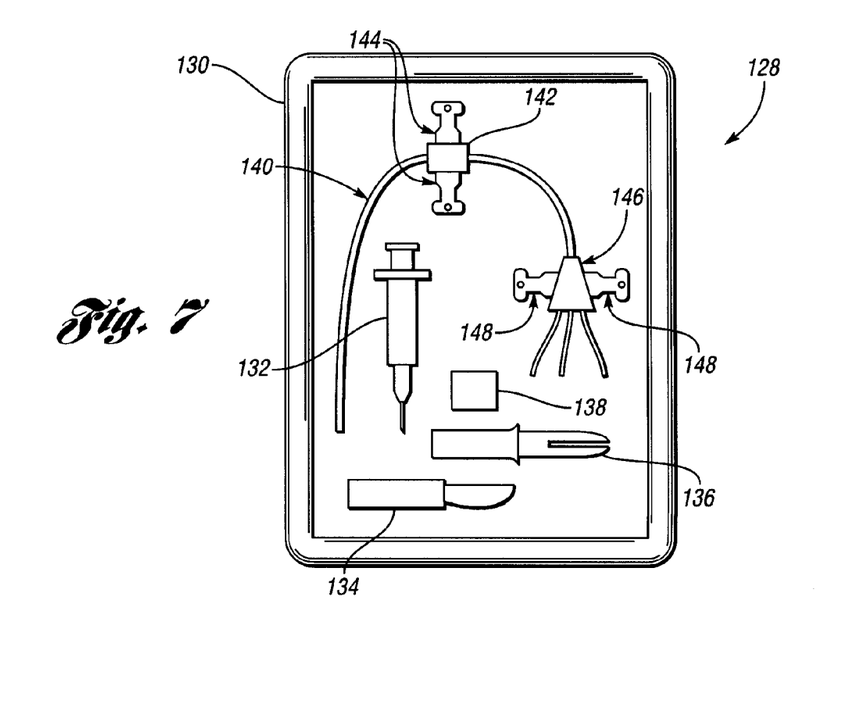
FIG. 7 is a top plan view of a catheter kit in accordance with the present invention.

FIG. 7 shows a catheter kit 128 in accordance with one embodiment of the present invention. The catheter kit 128 includes a package 130 that is configured to house a plurality of medical devices, such as a syringe 132, a scalpel 134, a staple gun 136, and a package of staples 138. In addition, the catheter kit includes a three-lumen catheter 140. It is understood that the medical devices in the kit 128 are shown partially schematically, and that the catheter 140 is not shown in its entirety. The catheter 140 includes a catheter clamp 142 and fixation apparatus 144 such as those described above. Similarly, the catheter 140 includes a catheter hub 146 and fixation apparatus 148, also similar to those described above. As described in conjunction with the method illustrated in FIG. 6, medical personnel may choose to anchor the catheter 140 using the fixation apparatus 148 at the hub 146, or if more flexibility is desired, the catheter clamp 142 may be chosen. In addition to the medical devices shown in FIG. 7, the kit 128 may include other medical devices, such as needles and sutures used as a secondary or alternative means to secure the catheter clamp 142 or the hub 146 to a patient.

Figure 8:
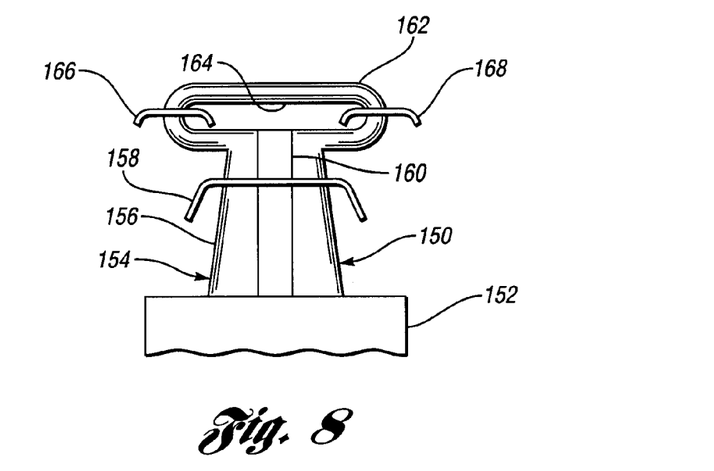
FIG. 8 is a partially fragmentary view of a medical device and fixation apparatus in accordance with another embodiment of the present invention.

FIG. 8 shows another embodiment of the present invention, and in particular, a fixation apparatus 150 attached to a medical device 152. Only a portion of the medical device 152 is shown in FIG. 8, however, it is understood that it could be a catheter clamp or other device as described herein. The fixation apparatus 150 includes an attachment feature 154, including an anchor receiving portion 156 configured to receive a non-suture anchoring device, such as a staple 158. The anchor receiving portion includes a ridge 160, configured similarly to the top portion 30 of the staple receiving portion 16 shown in FIG. 2. An anchor retaining end 162 is disposed at one end of the anchor receiving portion 156. The anchor retaining end 162 includes an aperture 164 that is generally elongated along a length of the anchor retaining end 162. This provides greater flexibility with regard to the placement of non-suture anchoring devices, such as staples 166, 168.

Figures 9, 11A:
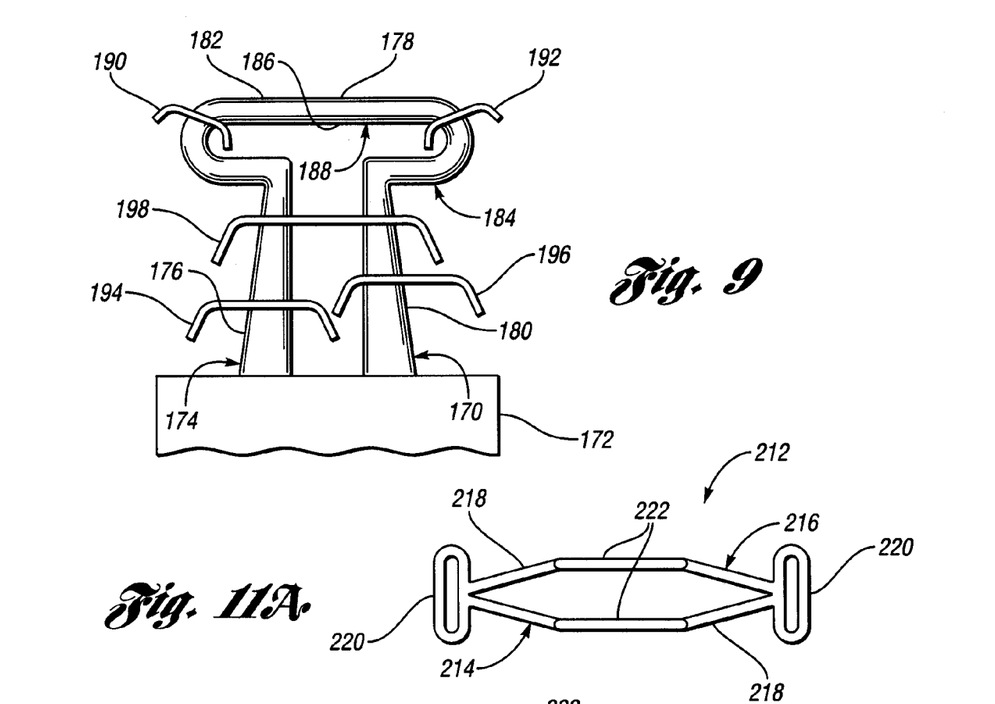
FIG. 9 is a partially fragmentary view of a medical device and fixation apparatus in accordance with another embodiment of the present invention.
FIG. 11A is a top plan view of a fixation apparatus attachable to a medical device in accordance with another embodiment of the present invention.

FIG. 9 illustrates a slightly different configuration of a fixation apparatus 170 attached to a medical device 172. The fixation apparatus 170 includes an attachment feature 174 that has an anchor receiving portion 176. At the end of the anchor receiving portion 176 is an anchor retaining end 178. The anchor receiving portion 176 includes an outer perimeter 180 that connects to a an outer perimeter 182 of the anchor retaining end 178. These two perimeters form a first contour 184. As shown in FIG. 9, the anchor receiving portion 178 includes an aperture 186 that is defined by a second contour 188 that is generally parallel to the first contour 184. This configuration also provides flexibility with regard to the placement of non-suture anchoring devices, such as staples 190, 192, 194, 196, 198.

Figure 10A:
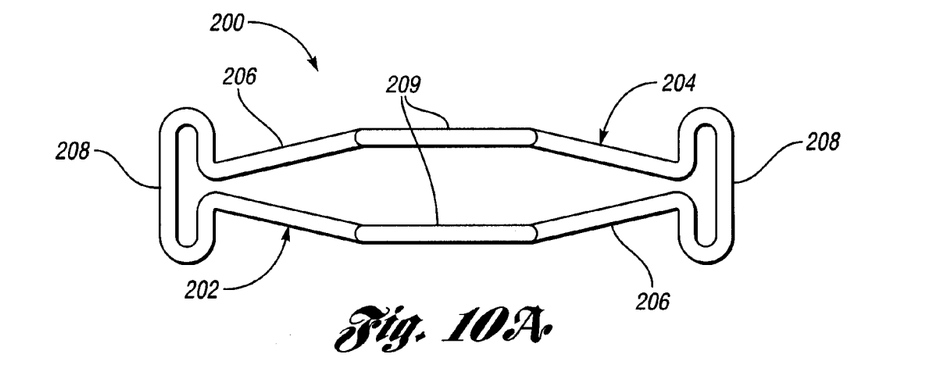
FIG. 10A is a top plan view of a fixation apparatus attachable to a medical device in accordance with another embodiment of the present invention.
Figure 10B:
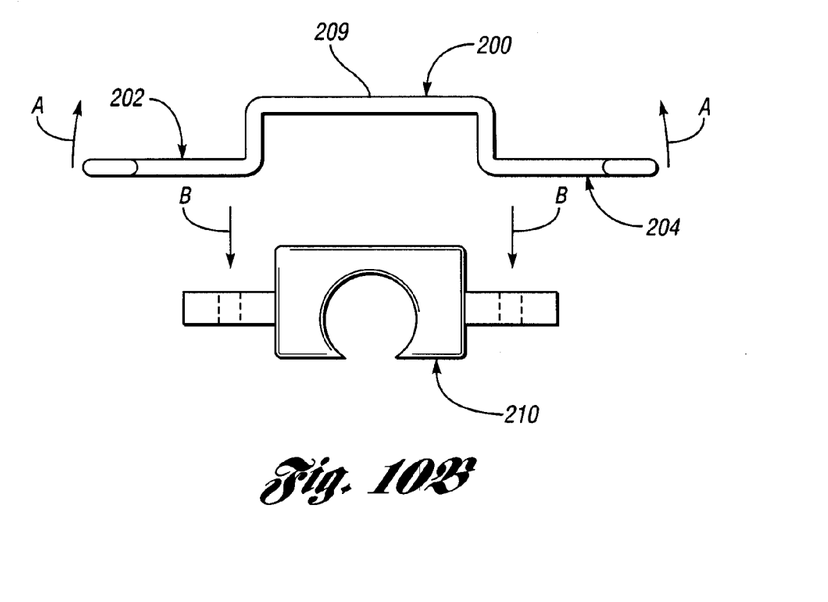
FIG. 10B is a side plan view of the fixation apparatus shown in FIG. 10A and a catheter clamp for use with the fixation apparatus.

FIG. 10A shows a top plan view of a fixation apparatus 200 in accordance with another embodiment of the present invention. The fixation apparatus 200 includes two attachment features 202, 204, each of which has an anchor receiving portion 206. Similar to other configurations described above, each of the anchor receiving portions 206 includes an anchor retaining end 208. In the embodiment shown in FIG. 10A, however, the fixation apparatus 200 further includes a clamp portion 209 disposed between the attachment features 202, 204, which is configured for attaching the fixation apparatus 200 to a medical device, such as a catheter clamp. This is illustrated in FIG. 10B where the curved arrows A-A illustrate the flexibility of the fixation apparatus 200, such that applying a force to move the attachment features 202, 204 in the direction of the arrows A-A opens the clamp portion 209 so that it can receive a medical device, such as catheter clamp 210. Releasing the force exerted on the attachment features 202, 204 secures the clamp portion 209 to the catheter clamp 210.

Figure 11B:
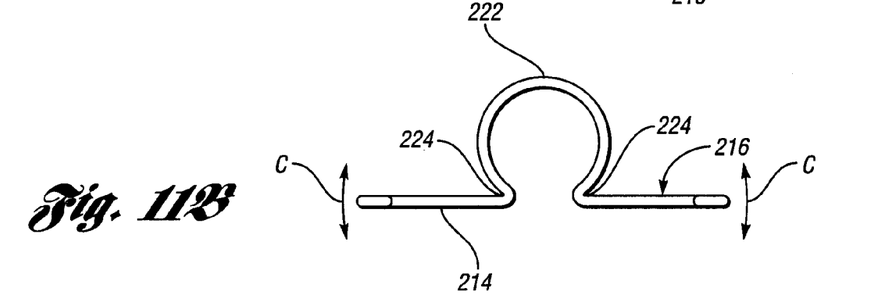
FIG. 11B is a side plan view of the fixation apparatus shown in FIG. 11A.
Figure 11C:
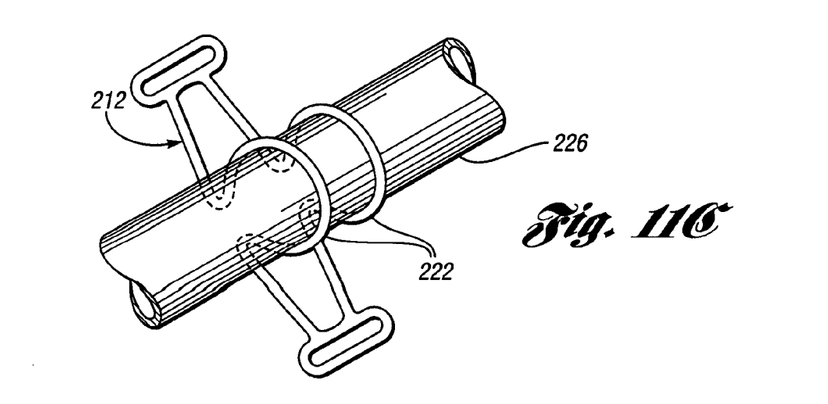
FIG. 11C is a perspective view of a catheter line having the fixation apparatus of FIGS. 11A and 11B attached thereto.

A variation of this configuration is illustrated in FIGS. 11A-11C. FIG. 11A shows a fixation apparatus 212 in accordance with another embodiment of the present invention. The fixation apparatus 212 includes two attachment features 214, 216, each of which has an anchor receiving portion 218. Each of the attachment features 214, 216 includes an anchor retaining end 220. The fixation apparatus 212 further includes a clamp portion 222 disposed between the attachment features 214, 216. In addition to the anchor retaining ends 220, each of the attachment features 214, 216 includes an anchor retaining end 224, which is formed as part of the clamp portion 222. The clamp portion 222 is configured for attaching the fixation apparatus 212 to a medical device, such as a catheter line 226—see FIG. 11C. The attachment mechanism is illustrated in FIG. 11B where the curved arrows C-C illustrate the flexibility of the fixation apparatus 212, such that applying a force to move the attachment features 214, 216 in the direction of the arrows C-C opens the clamp portion 222 so that it can receive a medical device, such as the catheter line 226. Releasing the force exerted on the attachment features 214, 216 secures the clamp portion 222 to the catheter line 226.

Figure 12:
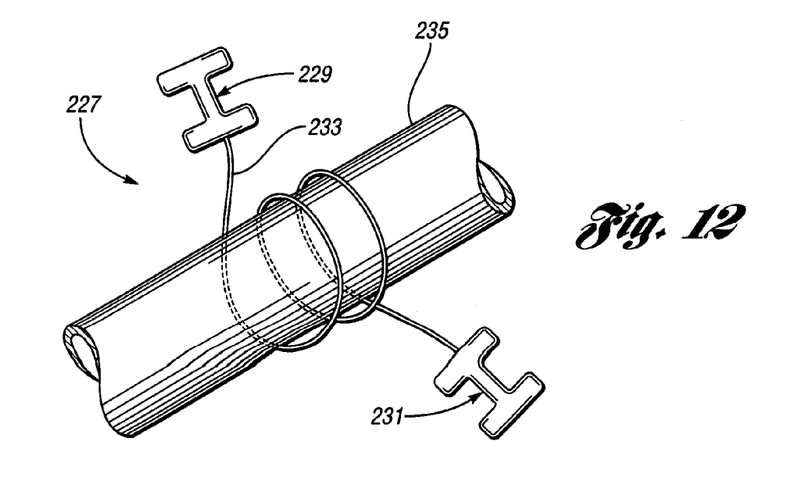
FIG. 12 illustrates a catheter line and fixation apparatus attachable to the catheter line in accordance with another embodiment of the present invention.

Another variation of the clamp configuration is illustrated in FIG. 12. In particular, FIG. 12 shows a fixation apparatus 227 in accordance with another embodiment of the present invention. The fixation apparatus 227 includes two attachment features 229, 231 attached to a flexible strap portion 233 that is configured to be wrapped around a medical device, such as a catheter line 235. The flexible strap portion 233 can be configured in the form of a wire, a flat ribbon, or some other configuration effective to provide the flexibility necessary to wrap the strap portion 233 around a medical device, such as the catheter line 235. The fixation apparatus 227 can be, for example, molded from a polymeric material, such as those described above. In such a case, the attachment features 229, 231 can be integrally molded with the strap portion 233. In other embodiments, for example, where the fixation apparatus 227 is made from a metallic material, the attachment features 229, 231 can be mechanically attached to the strap portion 233, for example, by soldering or crimping.

Figure 13:
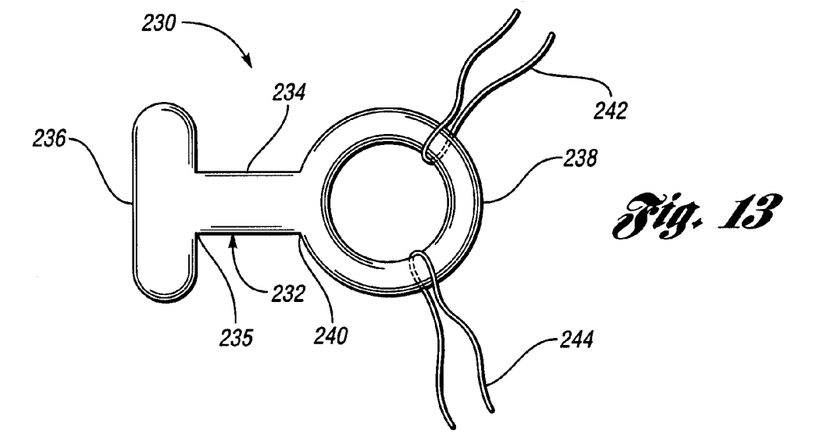
FIG. 13 shows a top plan view of a fixation apparatus in accordance with another embodiment of the present invention.

As described above, fixation apparatuses in accordance with the present invention can be used with different types of medical devices. A number of such devices were described and illustrated in the drawing figures. In addition to these types of medical devices, fixation apparatuses in accordance with the present invention can also be used in conjunction with other types of medical devices, for example, a suture. For example, FIG. 13 illustrates a fixation apparatus 230 in accordance with another embodiment of the present invention. The fixation apparatus 230 includes an attachment feature 232 having an anchor receiving portion 234. At one end 235 of the anchor receiving portion 234 is an anchor retaining end 236. At the other end 240 of the anchoring receiving portion 234 is a suture receiving portion 238.

In the embodiment shown in FIG. 13, the suture receiving portion 238 is configured as a closed polygonal structure—i.e., a circle. This allows one or more sutures, such as sutures 242, 244, to be attached to the suture receiving portion 238 for use by medical personnel without the need to use a needle on or near the patient. In particular, the fixation apparatus 230 can be affixed to a patient, either on the surface of the skin, as with the catheter clamps described above, or it can be used internally. For example, it may be desirable to tie a suture around a portion of a patient's organ, in a location where it is undesirable to anchor the suture directly to the patient. In such a case, a fixation apparatus, such as the fixation apparatus 230, can be stapled to a surrounding bone or hard tissue, thereby making sutures 242, 244 readily available without having to suture through an internal organ.

Figure 14:
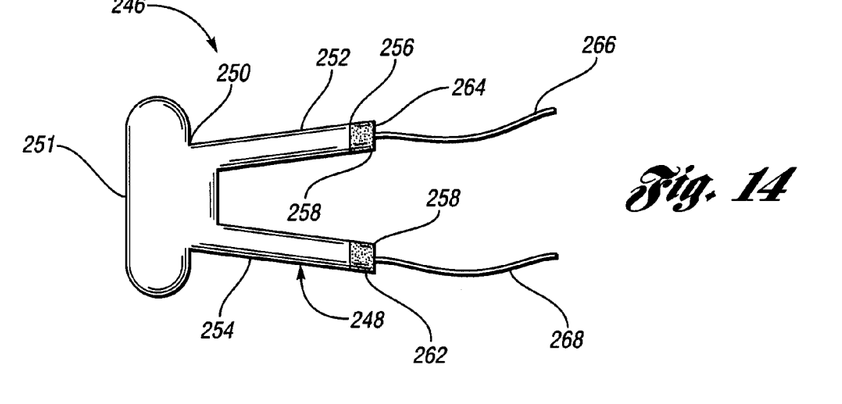
FIG. 14 shows a top plan view of a fixation apparatus in accordance with another embodiment of the present invention.

FIG. 14 illustrates a variation of the device shown in FIG. 13. In particular, a fixation apparatus 246 includes an attachment feature 248 having an anchor receiving portion 250. At the end of the anchor receiving portion is an anchor retaining end 251. Similarly, another anchor retaining end 256 is disposed at the other end of the anchor receiving portion 250. In the embodiment shown in FIG. 14, the anchor retaining end 256 does not have a solid structure such as the anchor retaining end 251, rather, it is formed from the widest part of the two legs 252, 254 which are spaced apart at a distance that is greater than a closed length of a staple configured to be attached to the anchor receiving portion 250. The attachment feature 250 includes a terminating end 258, which is formed from the two ends of the legs 252, 254. In the embodiment shown in FIG. 14, end caps 262, 264 are crimped onto the terminating end 258, to retain sutures 266, 268. Similar to the embodiment shown in FIG. 13, the fixation apparatus 246 may be conveniently used internally to a patient to allow the use of sutures where it may not be desirable to attach the suture directly to the patient.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A fixation apparatus for attaching a medical device to a patient, the fixation apparatus comprising:
    an attachment feature configured to cooperate with the medical device and at least one non-suture anchoring device to facilitate attachment of the medical device to the patient, the attachment feature including:
    an anchor receiving portion having a first dimension and including two ends, the anchor receiving portion being configured to receive the at least one non-suture anchoring device, wherein the two ends of the anchor receiving portion define a length, and a cross section of the anchor receiving portion taken perpendicularly to the length includes a first portion having a first width and a second portion adjacent the first portion and having a second width less than the first width, the second portion being disposed away from the patient relative to the first portion such that at least one open area exists between the anchor receiving portion and a non-suture anchoring device disposed around the anchor receiving portion, the at least one open area being above the first portion relative to the patient for facilitating removal of the non-suture anchoring device, and
    first and second anchor retaining ends respectively disposed adjacent one of the ends of the anchor receiving portion, each of the anchor retaining ends having a second dimension greater than the first dimension of the anchor receiving portion, thereby inhibiting the anchor receiving portion from dislodging from the at least one non-suture anchoring device when the at least one non-suture anchoring device is received by the anchor receiving portion.

2. The fixation apparatus of claim 1, wherein one of the anchor retaining ends includes a portion of the medical device.

3. The fixation apparatus of claim 1, wherein a cross section of the anchor receiving portion taken perpendicularly to the length has a width that is variable along at least a portion of the length.

4. The fixation apparatus of claim 3, wherein the anchor receiving portion includes a recess oriented generally transversely to the length and configured to cooperate with a non-suture anchoring device to inhibit movement of the fixation apparatus after the non-suture anchoring device is received by the anchor receiving portion.

5. The fixation apparatus of claim 1,
    wherein a cross section of the anchor receiving portion taken perpendicularly to the first width has a height that is variable along at least a portion of the length.

6. The fixation apparatus of claim 1, wherein the attachment feature includes an aperture disposed therethrough for receiving an anchoring device secondary to the non-suture anchoring device.

7. The fixation apparatus of claim 6, wherein the aperture is generally elongated along a length of the one of the anchor retaining ends.

8. The fixation apparatus of claim 1, further comprising:
    two of the attachment features; and
    a clamp portion disposed between the attachment features and configured for attachment to the medical device, the attachment features being attached to the clamp portion such that a force exerted on the attachment features opens the clamp portion to receive the medical device, and removal of the force biases the clamp portion against the medical device after the medical device is received in the clamp portion.

9. The fixation apparatus of claim 8, wherein the clamp portion is configured for attachment to a catheter clamp.

10. The fixation apparatus of claim 8, wherein the clamp portion is configured for attachment to a catheter line.

11. The fixation apparatus of claim 8, further comprising a suture receiving portion attached to the attachment feature and configured to receive at least one suture thereon.

12. The fixation apparatus of claim 11, wherein the suture receiving portion forms a closed polygonal structure for securing the at least one suture thereto.

13. The fixation apparatus of claim 11, wherein the attachment feature includes a terminated end forming at least a portion of the suture receiving portion.

14. The fixation apparatus of claim 1, further comprising:
two of the attachment features; and
a flexible strap portion disposed between the attachment features and configured to be wrapped around the medical device to attach the strap portion to the medical device.

15. A catheter clamp, comprising:
a tube retaining portion configured to receive a catheter line therein; and
an attachment feature configured to cooperate with the tube retaining portion and at least one surgical staple to facilitate stapling of the tube retaining portion to a patient, the attachment feature including:
a staple receiving portion including proximal and distal ends and a first dimension, the staple receiving portion being configured to receive the at least one surgical staple, the proximal end abutting the tube retaining portion, and
a retaining end disposed adjacent the distal end of the staple receiving portion, the retaining end having a second dimension greater than the first dimension of the staple receiving portion, thereby inhibiting the staple receiving portion from dislodging from the at least one staple when the at least one staple is received by the staple receiving portion;
wherein the retaining end and the tube retaining portion define a length, and a cross section of the staple receiving portion transverse to the length includes a first portion having a first width and a second portion adjacent the first portion and having a second width less than the first width, the second portion being disposed above the first portion such that at least one open area exists between the staple receiving portion and a staple disposed around the staple receiving portion, the at least one open area being above the first portion relative to the patient for facilitating removal of the staple.

16. The catheter clamp of claim 15, wherein a cross section of the staple receiving portion taken perpendicularly to the length has a width that is variable along at least a portion of the length.

17. The catheter clamp of claim 16, wherein the staple receiving portion includes a recess oriented generally transversely to the length and configured to cooperate with a staple to inhibit movement of the fixation apparatus after the staple is received by the staple receiving portion.

18. The catheter clamp of claim 15,
wherein a cross section of the staple receiving portion taken perpendicularly to the first width has a height that is variable along at least a portion of the length.

19. The catheter clamp of claim 15, wherein the attachment feature includes an aperture disposed therethrough for receiving an anchoring device secondary to the staple.

20. A fixation apparatus for attaching a medical device to a patient, the fixation apparatus comprising:
an attachment feature configured to cooperate with the medical device and at least one non-suture anchoring device to facilitate attachment of the medical device to the patient, the attachment feature including:
an anchor receiving portion having a first dimension and including two ends, the anchor receiving portion being configured to receive the at least one non-suture anchoring device,
first and second anchor retaining ends respectively disposed adjacent one of the ends of the anchor receiving portion, each of the anchor retaining ends having a second dimension greater than the first dimension of the anchor receiving portion, thereby inhibiting the anchor receiving portion from dislodging from the at least one non-suture anchoring device when the at least one non-suture anchoring device is received by the anchor receiving portion, a perimeter of the anchor receiving portion and a perimeter of one of the anchor retaining ends defining a first contour, and
an aperture disposed therethrough for receiving an anchoring device secondary to the non-suture anchoring device, the aperture in the attachment feature being defined by a second contour generally parallel to the first contour.

21. The fixation apparatus of claim 20, further comprising:
two of the attachment features; and
a clamp portion disposed between the attachment features and configured for attachment to the medical device, the attachment features being attached to the clamp portion such that a force exerted on the attachment features opens the clamp portion to receive the medical device, and removal of the force biases the clamp portion against the medical device after the medical device is received in the clamp portion.

22. The fixation apparatus of claim 20, wherein the two ends of the anchor receiving portion define a length, and a cross section of the anchor receiving portion taken perpendicularly to the length has a width that is variable along at least a portion of the length.

23. A fixation apparatus for attaching a medical device to a patient, the fixation apparatus comprising:
two attachment features configured to cooperate with the medical device and at least one non-suture anchoring device to facilitate attachment of the medical device to the patient, each of the attachment features including:
an anchor receiving portion having a first dimension and including two ends, the anchor receiving portion being configured to receive the at least one non-suture anchoring device, and
first and second anchor retaining ends respectively disposed adjacent one of the ends of the anchor receiving portion, each of the anchor retaining ends having a second dimension greater than the first dimension of the anchor receiving portion, thereby inhibiting the anchor receiving portion from dislodging from the at least one non-suture anchoring device when the at least one non-suture anchoring device is received by the anchor receiving portion; and
a flexible strap portion disposed between the attachment features and configured to be wrapped around the medical device to attach the strap portion to the medical device.

24. The fixation apparatus of claim 23, wherein the two ends of each respective anchor receiving portion define a length, and a cross section of each anchor receiving portion taken perpendicularly to its length has a width that is variable along a least a portion of the length.

25. The fixation apparatus of claim 24, wherein each anchor receiving portion includes a respective recess oriented generally transversely to its length and configured to cooperate with a non-suture anchoring device to inhibit movement of the fixation apparatus after the non-suture anchoring device is received by the respective anchor receiving portion.

* * * * *